(12) United States Patent
Saikalis et al.

(10) Patent No.: US 6,640,626 B2
(45) Date of Patent: Nov. 4, 2003

(54) METHOD AND SYSTEM FOR IDENTIFYING A TYPE OF GAS

(75) Inventors: George Saikalis, West Bloomfield, MI (US); Shigeru Oho, Farmington Hills, MI (US); Takashi Kadohiro, Livonia, MI (US)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/051,318

(22) Filed: Jan. 18, 2002

(65) Prior Publication Data

US 2003/0136175 A1 Jul. 24, 2003

(51) Int. Cl.⁷ ................................................. G01F 1/68
(52) U.S. Cl. ................................................. 73/204.11
(58) Field of Search .......................... 73/861.52, 861.51, 73/204.15, 204.17, 204.19, 204.21, 861.63, 861.64, 204.11, 23.2, 23.24, 23.25, 35.02, 53.05, 53.06

(56) References Cited

U.S. PATENT DOCUMENTS

| 4,542,640 | A | * | 9/1985 | Clifford | ..................... 73/31.06 |
| 4,907,441 | A | * | 3/1990 | Shurmer | ..................... 73/23.2 |
| 5,099,697 | A | * | 3/1992 | Agar | ............................ 73/195 |
| 5,415,024 | A | * | 5/1995 | Proffitt et al. | ............ 73/861.04 |

* cited by examiner

*Primary Examiner*—Harshad Patel
(74) *Attorney, Agent, or Firm*—Gifford, Krass, Groh, Sprinkle, Anderson & Citkowski, P.C.

(57) ABSTRACT

A method and a system are disclosed for identifying a gas type. The system includes a first sensor in contact with the gas and which produces a first electrical output signal indicative of a first condition of the gas. Similarly, a second sensor is also in contact with the gas and produces a second electrical output signal indicative of a second condition of the gas. A processor receives the output signals as input signals from the first and second sensors and determines the type of gas by calculation or from lookup tables stored in memory accessible to the processor. The first and second conditions of the gas are selected from the group of temperature, mass flow rate, temperature and pressure.

20 Claims, 6 Drawing Sheets

METHOD AND SYSTEM FOR IDENTIFYING A TYPE OF GAS

BACKGROUND OF THE INVENTION

I. Field of the Invention

The present invention relates to both a system and method for identifying a type of gas.

II. Description of the Prior Art

Many modern day vehicles utilize a combustible gaseous fuel in lieu of, or in addition to, a liquid fuel system. Such liquid fuel systems typically include both gasoline as well as diesel fuels.

There are currently several different types of gaseous fuels utilized with motor vehicles. For example, such currently utilized gaseous fuels include both propane and methane or mixtures thereof.

In order to provide for the efficient combustion of the fuel within the gaseous fuel engine, it is necessary to monitor the mass flow rate or velocity of the gaseous fuel to the engine. In order to obtain this information, mass flow sensors, also known as hot wire or hot element flow sensors, are fluidly connected in series between the source of the gaseous fuel and the engine so that the gaseous fuel flows through the flow meter. The flow meter then produces an electrical output signal proportional to the mass flow rate of the gaseous fuel and this output signal is coupled as an input signal to a microprocessor based electronic control unit (ECU) which controls the engine combustion for the vehicle. Such control of the engine combustion is necessary to not only maximize fuel efficiency, but also to minimize any noxious emissions.

These previously known hot wire mass flow sensors, however, inherently produce a nonlinear output signal in response to the gaseous flow through the sensor. Consequently, the previously known gas flow sensors are conventionally designed for a predetermined type of gas, for example a gas flow sensor for propane or a gas flow sensor for methane, and each flow sensor utilizes its own unique calibration curves to determine the actual mass flow rate from the output of the mass flow sensor. Furthermore, conventional hot wire sensors utilize a bridge circuit and an internal resistor to compensate for temperature variations. This internal temperature resistance compensation, however, varies from one gas to another type of gas. Consequently, a mass flow rate through these previously known hot wire mass flow sensors will vary depending upon the type of gas even for the same mass flow rate through the sensor.

In order to achieve efficient, pollution free and, indeed, safe operation of an internal combustion engine, the type of gaseous fuel utilized in the engine must be known by the ECU before the ECU can control the proper engine combustion for the engine. Consequently, most gaseous fuel internal combustion engines are designed and calibrated for a single type of gaseous fuel. However, there are situations where the wrong type of gaseous fuel may be supplied to the gaseous fuel engine or other situations in which operation of the engine by using two or even more different types of gaseous fuels is desirable such as liquid propane gas and compressed natural gas.

The identification of the gas type is also desirable in other types of gaseous systems, such as fuel cell applications.

Today, there are no known systems or methods for determining the type of gaseous fuel provided to an internal combustion engine.

SUMMARY OF THE PRESENT INVENTION

The present invention provides both a method and system for identifying the type of gas provided to an internal combustion engine or other gaseous systems.

In brief, the system of the present invention comprises a first sensor in contact with the gas. This first sensor provides a first electrical output signal indicative of a first condition of the gas.

Similarly, a second sensor is also in contact with the gas. This second sensor also provides a second output signal indicative of a second condition of the gas. The first and second conditions may be the same gas characteristic, e.g. the mass flow rate of the gas, but utilizing flow sensors with different calibrations.

The output signals from both of the sensors are coupled as input signals to a microprocessor based processing means. The processing means then compares the outputs from the sensor, often at two or more different operating conditions, to presorted lookup tables from which the gas type can be determined. Alternatively, the processing means can determine the gas type by calculation based upon the output signals from the sensors.

Furthermore, the first and second conditions of the gas are selected from the group of temperature, mass flow rate (which is directly proportional to gas velocity), temperature and pressure.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF PREFERRED EMBODIMENTS OF THE PRESENT INVENTION

BACKGROUND

Figure 1:
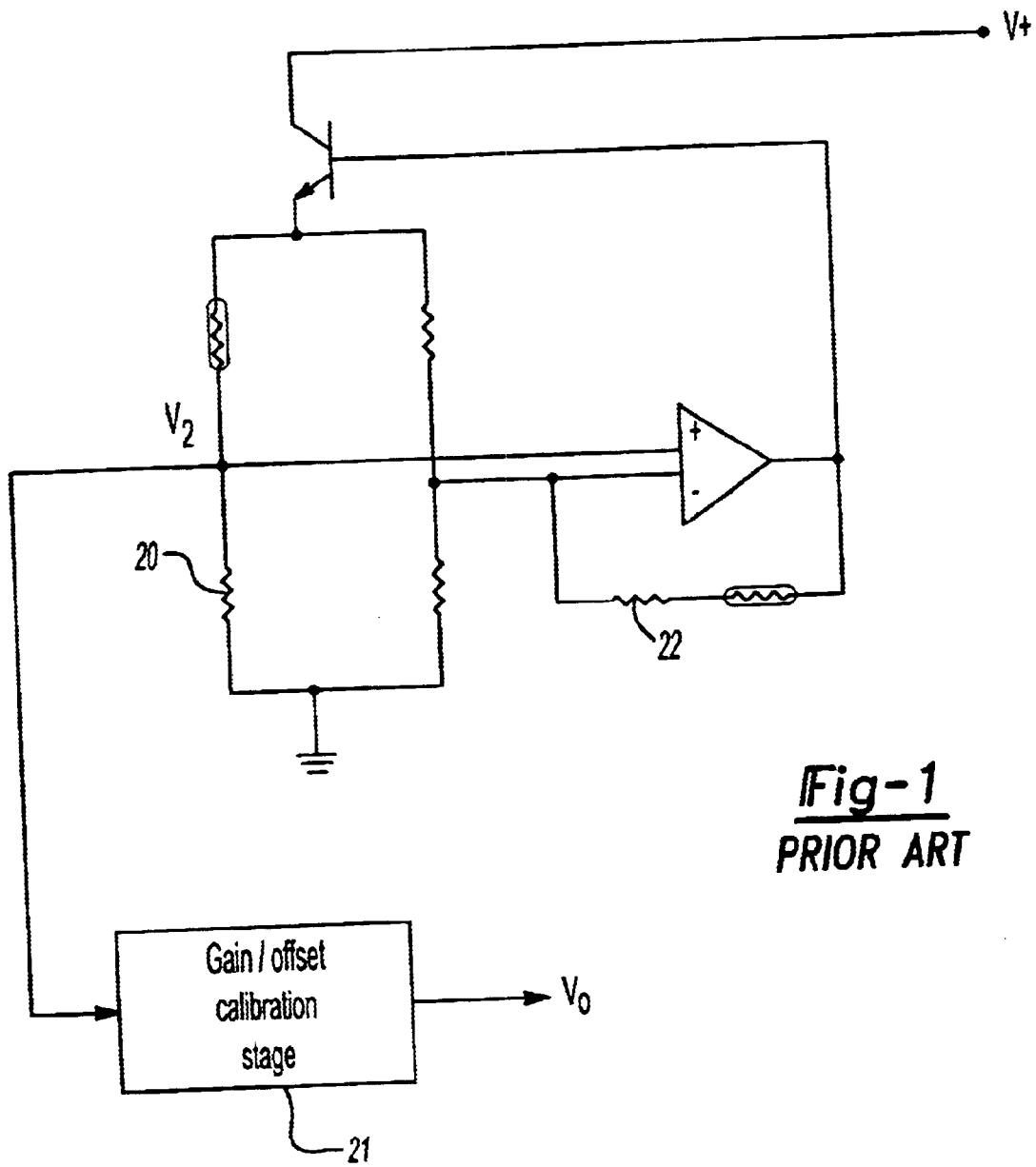
FIG. 1 is a schematic view illustrating a simplified conventional hot element current control circuit.
Figure 2:
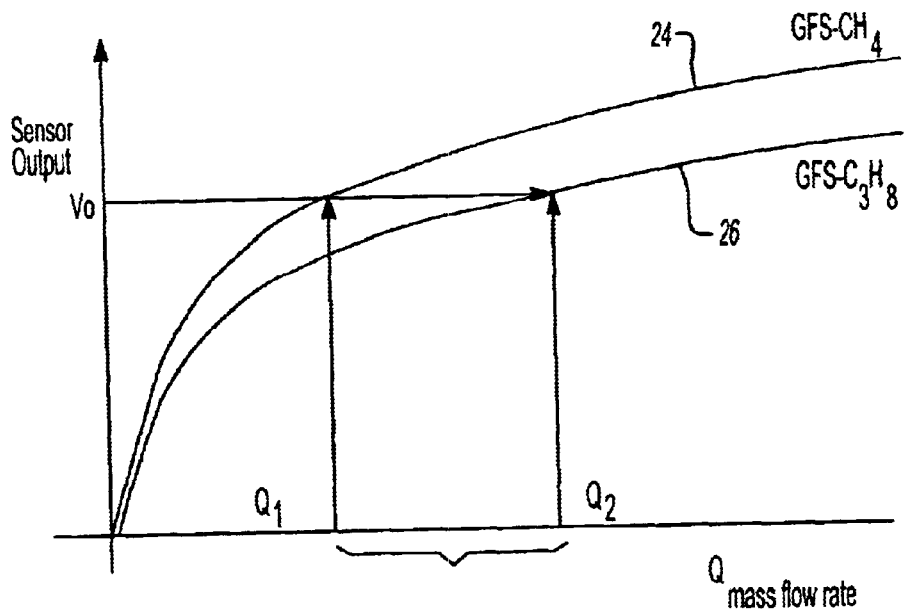
FIG. 2 is a graph illustrating the sensor output as a function of flow rate for two different gas types.

With reference first to FIGS. 1 and 2, in FIG. 1 a schematic for a conventional hot element or hot wire air flow sensor is there shown which produces an output signal $V_O$ which is proportional to the mass flow rate, or velocity, of the gaseous fuel through the flow meter.

With reference now particularly to FIG. 1, the output voltage $V_2$ from the gas flow sensor is conventionally measured across a 10 ohm resistor 20 for calculation ease. Furthermore, the mass flow sensor utilizes a bridge circuit and a gain/offset calibration stage 21 to output the output voltage $V_O$ and this bridge circuit includes an internal temperature compensation resistor 22. The internal compensation resistor 22 will vary as a function of the gas type. For example, if the gas flow sensor is designed to detect the flow of methane gas, the temperature compensation resistor 22 is approximately 17.5 ohms for the circuit illustrated in FIG. 1. Conversely, the temperature compensation resistor 22 for a mass flow sensor designed to measure the mass flow rate of propane would be approximately 32 ohms.

FIG. 2 graphically illustrates the output $V_O$ as a function of the mass flow rate Q for a mass flow sensor with the same temperature compensation resistor 22 but for two different gases. Specifically, graph 24 illustrates the output of $V_O$ from the sensor as a function of mass flow rate Q for methane while graph 26 illustrates the output from the mass flow sensor as a function of mass flow rate Q for the gas propane.

As can be seen from FIG. 2, at a first mass flow rate $Q_1$ for the gas methane, the mass flow sensor provides an output signal $V_O$. This same voltage output signal $V_O$, however, also occurs at a different flow rate $Q_2$ where the gas is propane, rather than methane. Consequently, the mass flow rate from the flow meter can only be determined from the output $V_O$ from the mass flow rate sensor when the type of gas is also identified.

As explained more fully hereinafter, the first detection method utilizes two independent mass flow rate sensors wherein one sensor has internal temperature compensation for a preselected gas, such as methane, while the other sensor has internal temperature compensation for a different preselected gas, such as propane.

Most conventional hot wire or hot element mass flow sensors utilize a heated element which transfers heat to the gas flow through the sensor. A bridge circuit, like the circuit shown in FIG. 1, maintains the temperature differential between the hot element and the temperature of the gas at a predetermined constant amount, typically 200° C., by varying the current flow through the heated element. The voltage output signal $V_O$ is then derived from the variable current by passing the variable current through the resistor 20 (FIG. 1).

The heat transfer coefficient h from the heated element to the gas flow through the mass flow sensor is determined by King's law which is reproduced below:

$$h = s_h \left[ C1 + C2 \left( \frac{u \cdot D}{v(T_F)} \right)^\beta \right] \frac{\lambda(T_F)}{D}$$

Where:

| | |
|---|---|
| C1 and C2: | Constants |
| $s_h$: | Surface area of the hot wire ($\pi \cdot D \cdot L$) |
| u: | Gas velocity [m/s] |
| D: | Hot wire diameter [m] |
| $v(T_F)$: | Kinematic viscosity [m²/s] |
| $\lambda(T_F)$: | Thermal conductivity [W/m · K] |
| $T_F$: | Hot wire surface (film) temperature [K.] |
| L: | Hot wire length [m] |
| $\beta$: | Empirically determined constant |

As can be seen from King's law above, there is a direct relationship between the gas velocity, gas kinematic viscosity, the gas thermal conductivity and the heat transfer coefficient. Furthermore, the kinematic viscosity ($v(T_F)$) and the thermal conductivity ($\lambda(T_F)$) vary as both a function of the gas temperature as well as the gas type.

The thermal convection or power transfer from the hot element to the gas in the mass flow sensor is determined by the following equation:

$$P = h \cdot \Delta T$$

Where: P=power, h=transfer coefficient from King's law, and $\Delta T$=temperature difference between the hot element and the ambient air (conventionally 200° centigrade).

The voltage output $V_O$ (FIG. 1) from the mass flow sensor is proportional to the electric power dissipated into the hot element. That electrical power, in turn, is proportional to the current flow through the hot wire.

If we assume the following:

$$\Delta T = 200° \text{ C.}$$

$$T_A = 20° \text{ C.}$$

where $T_A$=ambient gas temperature and $$P = h \cdot \Delta T$$
$$= 200h$$
$$= i^2 R_H$$

where $R_H$=resistance of hot element and $$V_2 = R_{20} i$$
$$= 10i$$

where:

$R_{20}$=resistance of resistor 20=10 ohms i=current through hot element.

The resistance of the hot element is then defined by the following equation:

$$R_H = R_O (1 + \alpha T_H) = 18.56(1 + 0.00387*220) = 34.37 \Omega$$

where $R_O$=resistance of hot element at ambient temperature.

Therefore, for a balanced hot element bridge control circuit such as illustrated in FIG. 1, the output $V_2$ from the hot element sensor can be derived as follows:

$$V_2 = 10 \sqrt{\frac{200h}{R_H}} = 10 \sqrt{\frac{200h}{34.47}} = 24.123 \sqrt{h}$$

Consequently, the output voltage from the mass flow sensor is dependent upon the electrical current flowing through the heated element which also flows through the resistor 20 in FIG. 1. In turn, the electrical current through the heated element is proportional to the velocity across the heated element. Furthermore, the differences in both the kinetic viscosity as a function of the gas temperature as well as the thermal conductivity as a function of the gas temperature both vary as a function of the gas type.

Detection Method 1

With the foregoing background information and with reference to FIG. 3, the first gas type detection method will now be described in greater detail. As shown diagrammatically in FIG. 3, a system 30 of the present invention is there shown having a flow conduit 31 positioned in series between a pressurized gas source 32 and a gas outlet 34 which is fluidly connected to the combustion engine, fuel cells, or other gaseous system. Furthermore, as is clear from FIG. 3, all of the gas flow to the engine, fuel cell or other gas consuming device flows through the conduit 31.

The first detection method utilizes a first heated element mass flow sensor 40 having internal temperature compensation for a preselected gas type, such as propane. The heated element 42 for the sensor 40 is disposed in contact with the gaseous flow from the source 32 and to the outlet 34 so that the heated element 42 transfers heat to the gaseous flow in the fashion described above. Furthermore, the sensor 40 provides an output signal $V_O$ to a microprocessor based processing unit 44 through an electrical connection 46 indicative of a first condition of the gas, i.e. the mass flow rate of the gas utilizing a mass flow sensor calibrated for a first preselected gas type. The processing unit 44 inputs this output signal 42 from the sensor 40 utilizing conventional electronic circuitry, such as analog to digital converters.

Figure 3:
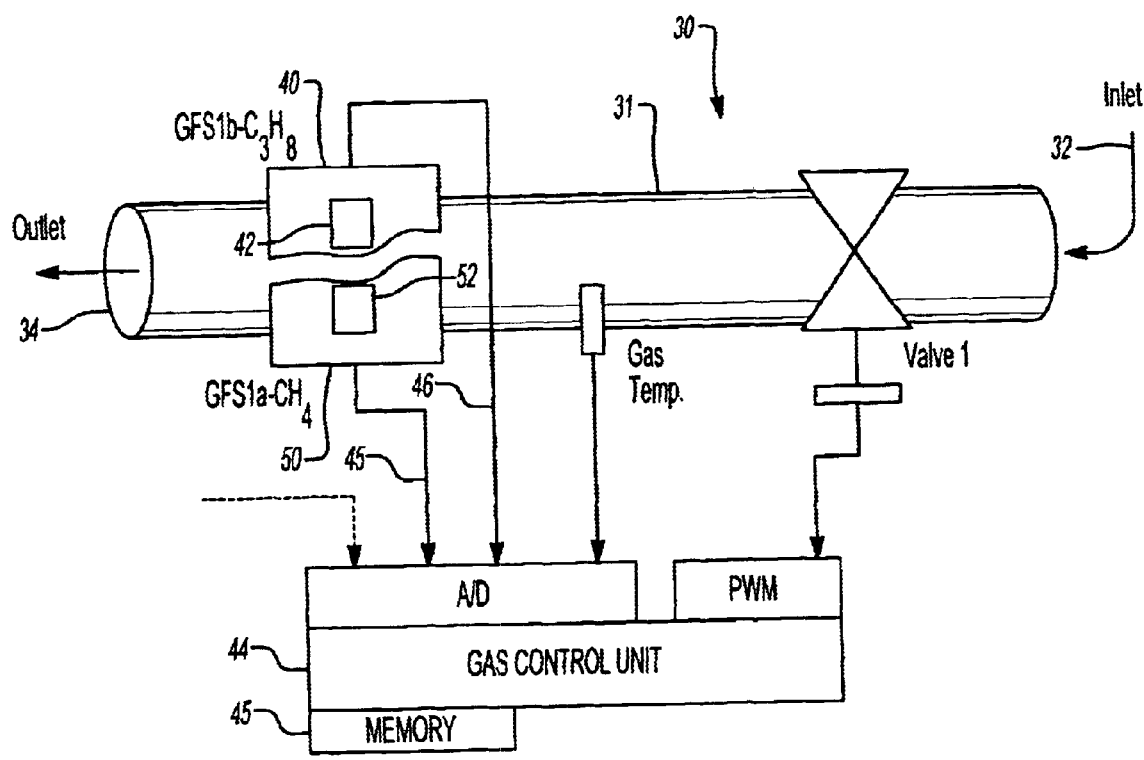
FIG. 3 is a diagrammatic view illustrating a first preferred embodiment of the present invention.

Still referring to FIG. 3, the first detection method also utilizes a second heated element mass flow sensor 50 having internal temperature compensation for a second preselected gas type, such as methane. The second sensor 50 has a hot element 52 in contact with the gas which provides an output signal $V_O'$ as an input signal to the processing means 44 on line 45 indicative of a second condition of the gas, i.e. the mass flow rate of the gas utilizing a mass flow sensor calibrated for the second preselected gas type. However, since the sensors 40 and 50 have different internal temperature calibration and compensation, for the same flow from the source 32 and to the outlet 34, the voltage outputs $V_O$ and $V_O'$ from the sensors 40 and 50, respectively, will differ from each other due to their different internal trim or calibration and temperature compensation. The hot wires 42 and 52 for the sensors 40 and 50, however, are placed within the same bore size of the conduit 31 so that voltage output readings $V_O$ and $V_O'$ from the sensors 40 and 50, respectively, may be made essentially simultaneously at the same mass flow rate through the conduit 31.

For the first sensor 40 calibrated with propane, the voltage output $V_O$ from the sensor 40 calibrated for propane may be representative as a simplification of King's law in the following fashion:

$$V_O = Au^\beta + B$$

where u=air velocity and the β variable empirically determined at 0.35.

Similarly, the output signal $V_O'$ from the second sensor 50 may also be represented in the following simplified manner:

$$V_O' = A'u^\beta + B'$$

Where:

A=f(G, O, λ, v, $T_H$, $T_A$)
B=f(G, O, λ, v, $T_H$, $T_A$)
A'=f(G', O', λ, v, $T_H$, $T_A$)
B'=f(G', O', λ, v, $T_H$, $T_A$)

Where G, O, G', O' are the gains and offsets of the circuit output stage, i.e. the internal calibration and temperature compensation for the two flow sensors 40 and 50.

The ratios A/B and A'/B' are known ratios. Consequently, the above equations produce the mathematical set of equations as follows:

$$V_1 = Au_1^\beta + B$$

$$V_2 = Au_2^\beta + B$$

and $$V_1' = A'u_1^\beta + B'$$

$$V_2' = A'u_2^\beta + B'$$

Where $V_1$=first voltage output from sensor 40 at a first air velocity $V_2$=voltage output from sensor 40 at a second air velocity $V_1'$=voltage output from the second sensor 50 at the first gas velocity $V_2'$=voltage output from the second sensor 50 at the second gas velocity The voltages $V_1$ and $V_2'$ are thus determined from the sensors 40 and 50, respectively, at a first gas velocity through the conduit 31. Similarly, the voltages $V_2$ and $V_2'$ represent the output voltages from the sensors 40 and 50, respectively, at a second and different gas velocity or mass flow rate through the conduit 31. These four output voltages $V_1$, $V_2$, $V_1'$ and $V_2'$ are coupled as input signals to the processing means and effectively represent four independent equations. As such, the unknown remaining four variables B, B', $u_1$ and $u_2$ can be solved by the microprocessor based processing means 44.

Specifically, through internal mapping, lookup tables and/or mathematical functions, the following is determined:

$$u_1 = f(V)$$

$$u_2 = f(V')$$

$$\Delta u = u_2 - u_1$$

where $u_1$=gas flow rate from the first sensor 40, $u_2$=gas flow rate from the sensor 50, and Δu=the difference between the mass flow rate $u_1$ and $u_2$ at a given time.

Figure 4:
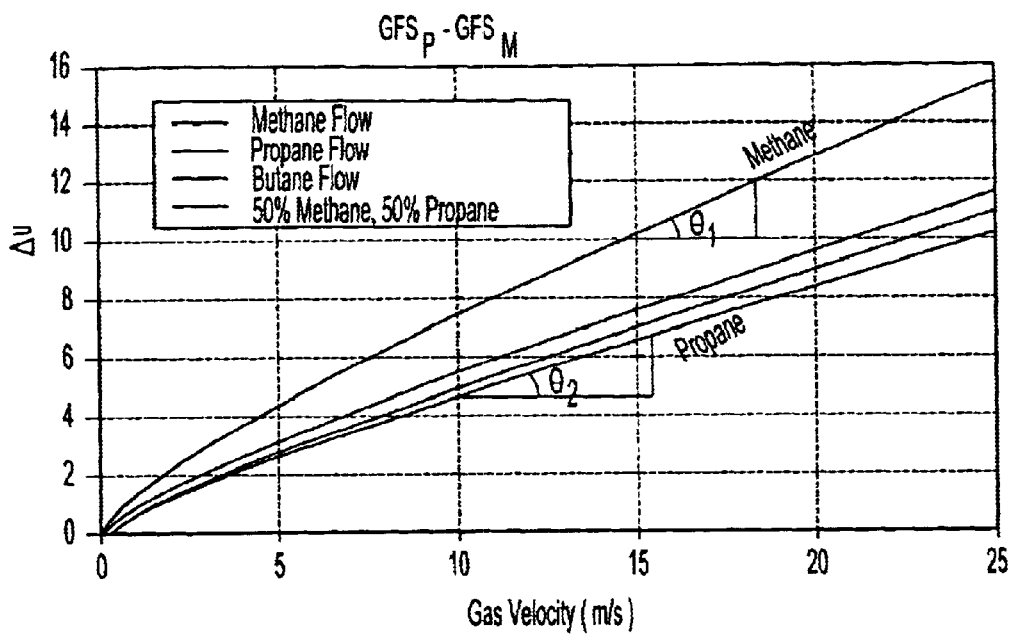
FIG. 4 is a graph illustrating the operation of the first preferred embodiment of the invention.

Thereafter, by making several sequential measurements from the sensors 40 and 50 at different times and at different gas velocities through the conduit 31, the calculated value Δu as a function of gas velocity may be graphed as illustrated in FIG. 4. From FIG. 4, it can therefore be seen that the quantity Δu, as well as the slope of the graph Δu, varies as a function of different gas types. The microprocessor based processing means 44, utilizing lookup tables stored in memory 45 (FIG. 3), mapping, or mathematical equations, then determines the type of gas as a function of both Δu and the slope of Δu.

Second Detection Method

Figure 5:
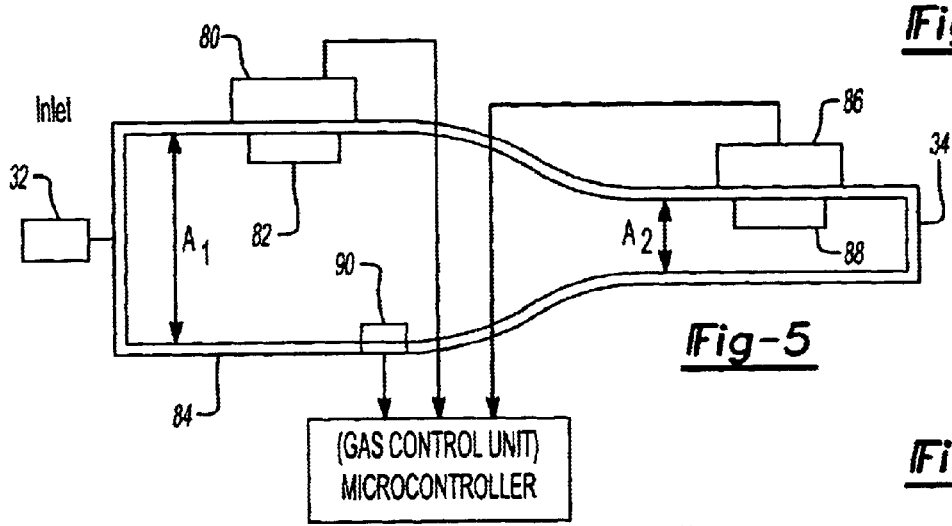
FIG. 5 is a diagrammatic view illustrating a second preferred embodiment of the invention.

With reference now to FIG. 5, in a second embodiment of the present invention, a first hot element mass flow transducer 80 has its hot element 82 positioned within the conduit 84 in contact with the gas between the source 32 and outlet 34. Similarly, a second heated element mass flow sensor 86 has its heated element 88 positioned in the conduit 84 in contact with the gas but in a portion of the conduit 84 having a different bore size than the portion of the conduit 84 in which the heated element 82 of the first sensor 80 is positioned. Both sensors 80 and 86 are calibrated for the same gas, e.g. methane, and both provide electrical output signals to the processing means 44. As before, the output signals $V_O$ from the sensor 80 and $V_{O'}$ from the second sensor 86 are proportional to the mass flow rate or gas velocity through the conduit 84.

A temperature sensor 90 also provides an electrical output signal to the processing means 44 representative of the temperature of the ambient gas flowing through the conduit 84.

Since the two gas flow sensors 80 and 86 are calibrated for the same type of gas, the gas flow rate versus voltage output calibration for these two sensors 80 and 86 will remain the same. However, the difference in bore size of the conduit 84 produces a velocity difference between the two flow sensors 80 and 86 for the same mass flow rate. Since the internal temperature compensation, i.e. the resistor 20 (FIG. 1) is the same for both sensors 80 and 86, King's law simplifies as follows:

$$h = s_h \left[ 2.4 + 1.6 \left( \frac{u \cdot D}{v(T_F)} \right)^\beta \right] \frac{\lambda(T_F)}{D}$$

with $V_2 = 24.123\sqrt{h}$ and $V_O = AV_2 + B$.

Which simplifies to $$V_O = 24.123 * A * \sqrt{C_1 + C_2 u^\beta} + B$$

By measuring the output velocities, we get the following set of equations:

$$V_o = 24.123 * A * \sqrt{C_1 + C_2 u_1^{0.35}} + B \quad u_1: \text{velocity in bore 1}$$

$$V_o' = 24.123 * A * \sqrt{C_1 + C_2 u_2^{0.35}} + B \quad u_2: \text{velocity in bore 2}$$

where $V_O$ is the output from sensor 80 while $V_{O'}$ is the output from the sensor 86.

As in the first embodiment of the invention, by utilizing multiple measurements from the gas flow sensors 80 and 86 at different flow rates through the conduit 84, the calculated value $\Delta u$, i.e. $u_2 - u_1$, as a function of gas velocity as well as the slope of $\Delta u$ may be determined and graphed as is shown in FIG. 4. The processing means 44, by utilizing mapping, lookup tables, or mathematical equations as well as the output from the temperature sensor 90 then estimates the gas type as a function of the value of $\Delta u$ and its slope.

Third Detection Method

Figure 6:
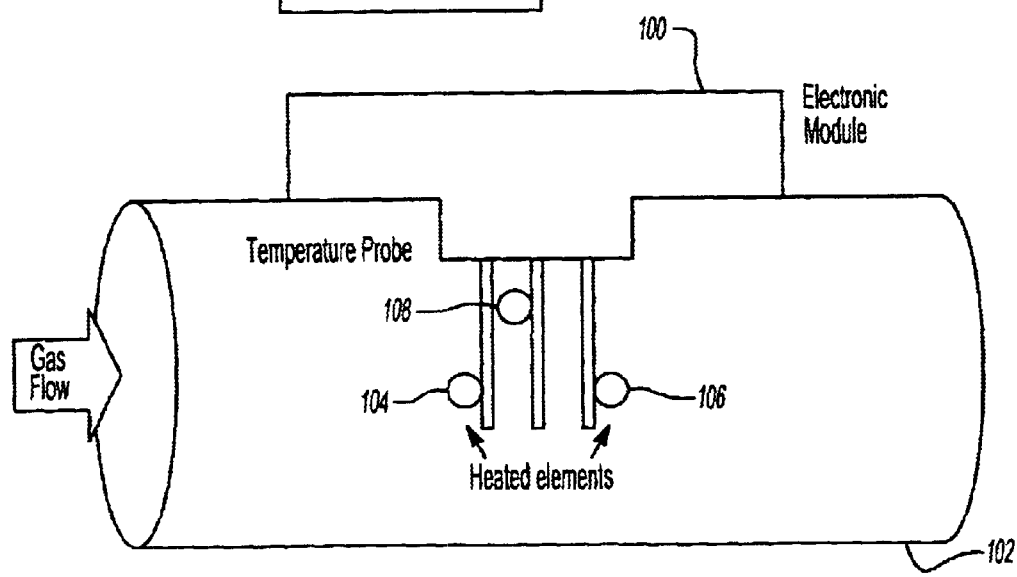
FIG. 6 is a diagrammatic view illustrating a third preferred embodiment of the invention.

With reference now to FIG. 6, a still further embodiment of the present invention is there shown in which a single gas flow sensor 100 is mounted to the conduit 102 through which the gas flows. Unlike the first embodiment of the invention, however, the flow sensor 100 utilizes two heated elements 104 and 106 as well as an ambient temperature sensor 108. Each heated element 104 and 106, furthermore, includes its own circuitry, like the type illustrated in FIG. 1, except that the heated elements 104 and 106 each have internal temperature compensation and trim for a specific and different type of gas. For example, the circuitry driving the heated element 104 may be trimmed and calibrated for methane while the heated element 106 may be calibrated and trimmed for a different gas, such as propane.

The third embodiment of the invention illustrated in FIG. 6 is thus essentially identical to the first embodiment of the invention illustrated in FIG. 3 except that instead of using two separate sensors 40 and 50 (FIG. 1), each calibrated for a different gas, the third embodiment of the invention utilizes a single sensor 100 having two discrete heated elements 104 and 106. However, the calculations and method for determining the type of gas for the third embodiment of the invention is substantially identical to the first embodiment of the invention and, for that reason, is incorporated by reference.

Fourth Detection Method

Figure 7:
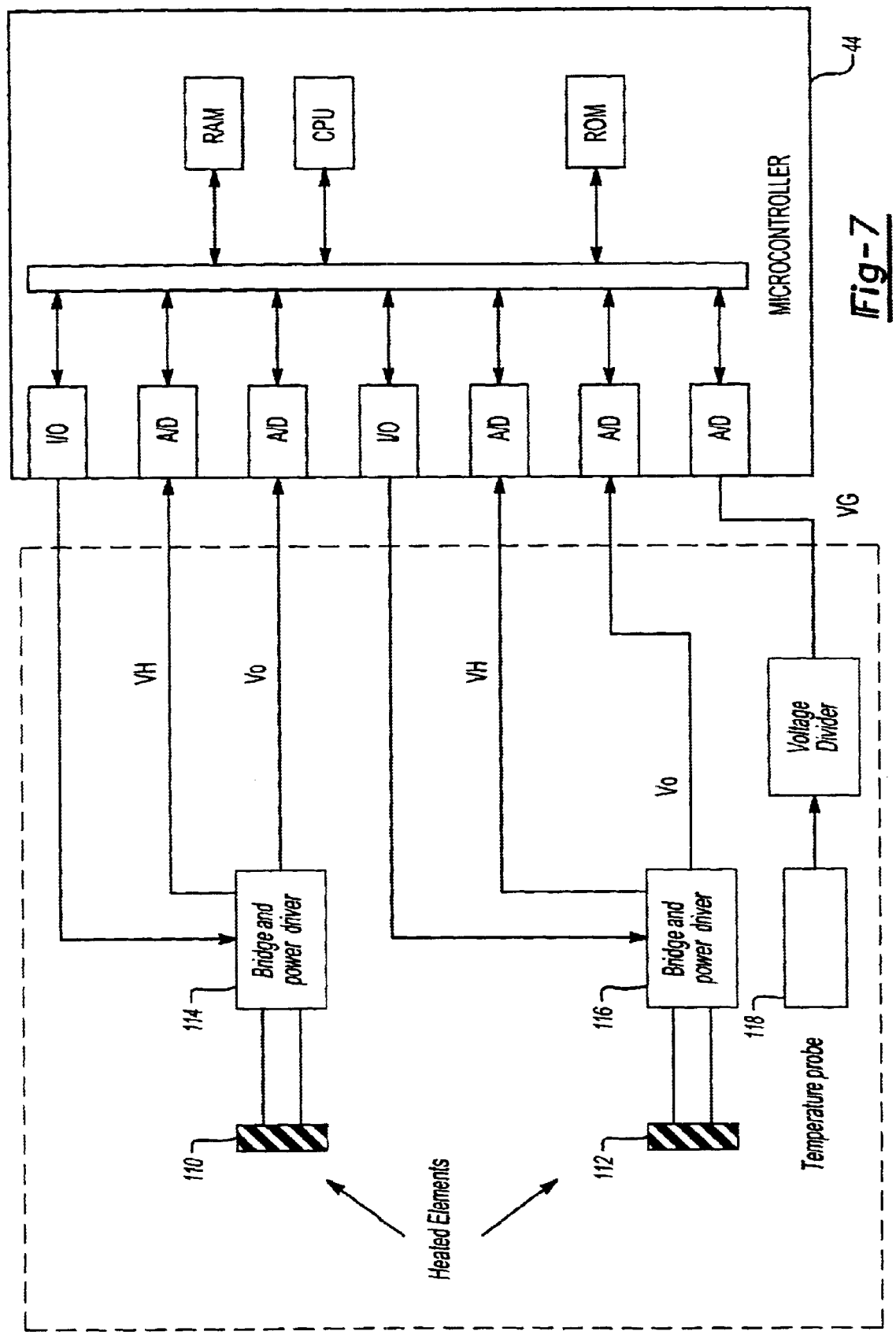
FIG. 7 is a diagrammatic view illustrating a fourth preferred embodiment of the invention.

With reference now to FIG. 7, a fourth embodiment of the present invention is there shown diagrammatically in which two different heated elements 110 and 112 are both disposed within the gas flow of the system. Each heated element 110 and 112 has its associated bridge and power driver 114 and 116, respectively, such that the outputs $V_O$ and $V_{O'}$ from the drivers 114 and 116, respectively, are proportional to the gas mass flow rate across the heated elements 110 and 112. These output signals $V_O$ and $V_{O'}$ are coupled as input signals to the microprocessor based processing means 44. Additionally, a temperature probe in contact with the gas in the system provides an electrical output signal proportional to the temperature of the ambient gas within the system. The output from the temperature probe 118 is also coupled as an input signal to the processing means 44.

In the first through third embodiments of the invention, the $\Delta T$ between the ambient air and the temperature of heated element was maintained at a constant 200° C. as is conventional. However, in the fourth embodiment of the invention in order to generate the four independent equations necessary to derive both the $\Delta u$ and the slope of $\Delta u$ in order to identify the type of gas, the $\Delta T$ between the ambient temperature and the first heated element 110 is maintained at a first difference, for example 200° C. Conversely, the $\Delta T$ between the ambient temperature and the second heated element 112 is maintained at a different amount, for example 160° C. By then taking multiple measurements, both $\Delta u$ and the slope of $\Delta u$ may be generated and, from that, the type of gas determined in the previously described fashions, i.e. by lookup tables, mapping or mathematical equations in computer memory accessible by the processing means 44.

Fifth Detection Method

Figure 8:
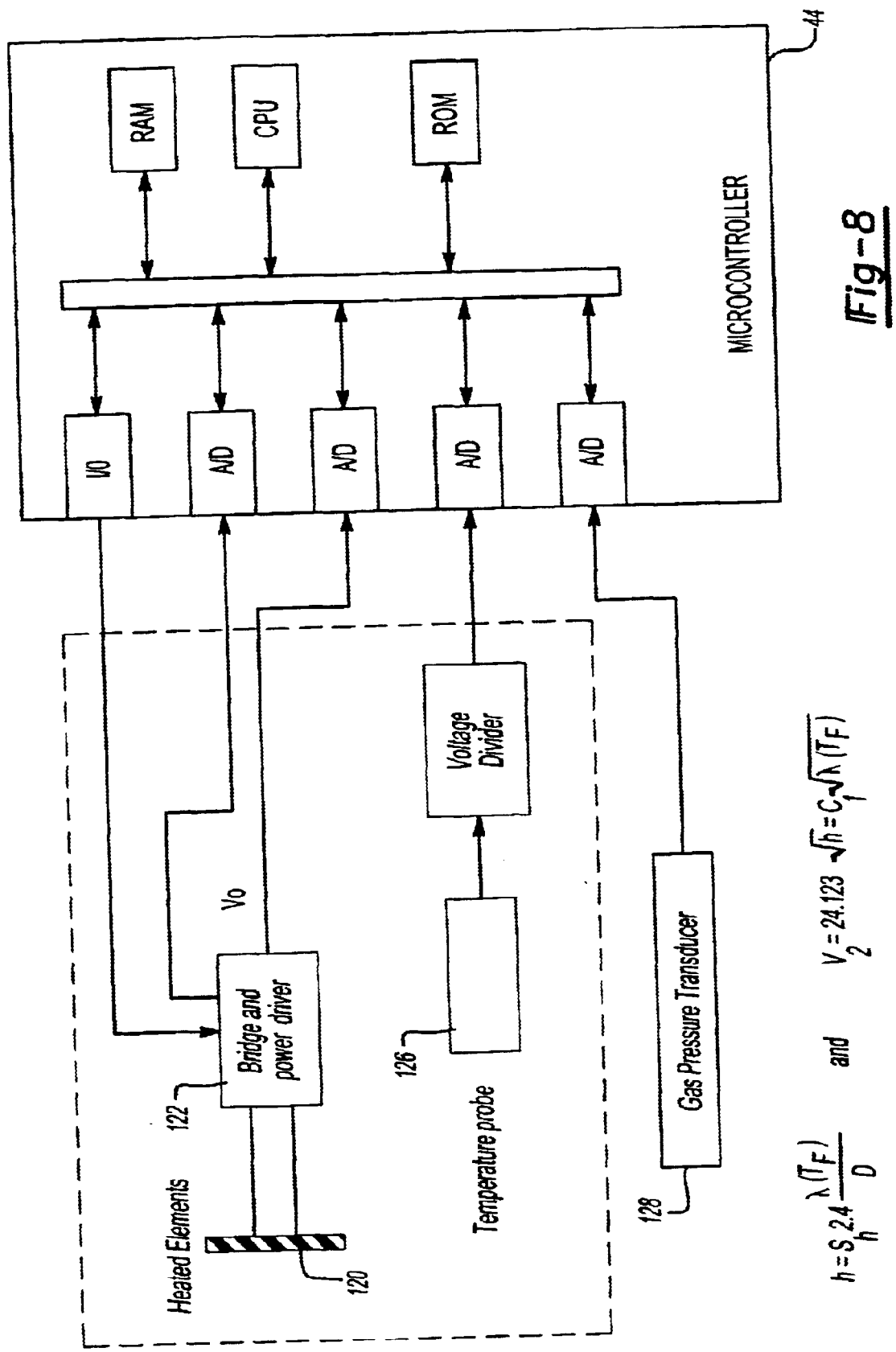
FIG. 8 is a diagrammatic view illustrating a fifth preferred embodiment of the invention.

With reference now to FIG. 8, a fifth embodiment of the invention is illustrated which is used for detecting the type of gas during a no flow gas condition. As shown in FIG. 8, the system includes a heated element 120 which is powered through a bridge and power driver 122. The bridge and power driver 122 provides an output signal $V_O$ to the processing means 44 as in the previously described fashion.

A temperature probe 126 also provides an electrical output signal as an input signal to the processing means 44 representative of the ambient temperature of the gas.

Unlike the previously known embodiments of the invention, however, a pressure transducer 128 is also in contact with the gas in the system and generates an electrical output signal to the processing means 44 representative of the gas pressure.

Since the gas flow rate (u) is set to zero, King's law simplifies and will be proportional to the thermal conductivity. In short, King's law simplifies to the following:

$$h = s_h 2.4 \frac{\lambda(T_F)}{D} \quad \text{and} \quad V_2 = 24.123\sqrt{h} = C_1\sqrt{\lambda(T_F)}$$

Thus, as the gas type changes, the thermal conductivity changes as well. However, since the thermal transfer to the gas is sensitive to the variation of density of the gas about the heated element, the gas pressure transducer 128 is required. As the pressure, and thus the density, of the gas increases, the losses from the hot element 120 to the gas increase so that the output voltage will likewise increase.

A processing means 44, by utilizing lookup tables, mapping or mathematical equations, is then able to determine the gas type by solving the above-identified simplification of King's law.

As a modification to this fifth embodiment of the invention, the temperature difference between the heated element 120 and the ambient air may be varied to obtain multiple data points. A slope is then calculated between those different points and the gas type is determined based upon that slope. Such lookup tables may be based upon either experimental or simulated values.

Sixth Detection Method

Figure 9:
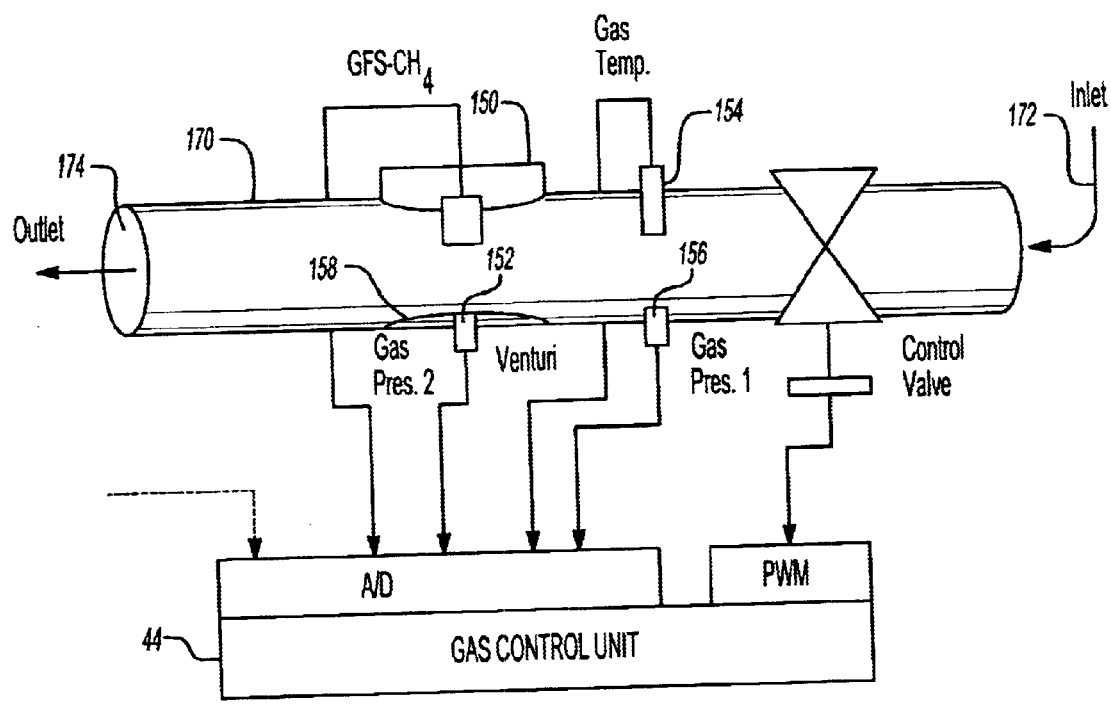
FIG. 9 is a diagrammatic view illustrating a sixth preferred embodiment of the invention.

With reference now to FIG. 9, a sixth embodiment of the present invention is there shown utilizing a hot element flow sensor 150, a temperature sensor 154 and two gas pressure sensors 152 and 156. All of the sensors 150, 152, 154 and 156 are disposed in a conduit 170 fluidly connected in series between the gas source 172 and outlet 174 and thus in contact with the gas flow. Each of these sensors 150–156 produce electrical output signals representative of their measured gas condition as input signals to the microprocessor based processing means 44.

Still referring to FIG. 9, the mass flow sensors 150 and pressure 152 are both disposed within a venturi 158 in the conduit 170 while the gas pressure sensor 156 is positioned upstream from the venturi 158.

The mass flow rate for both the heated element mass flow sensor 150 as well as the pressure sensor 152 are determined by the following:

$$Q_{GFS} = f(u, T_G)$$

$$Q_{pres} = f(P_1, P_2, d, T_G)$$

where Q is the mass flow rate, u is the mass flow velocity, $P_1$ is the pressure at the pressure transducer 156, $P_2$ is the pressure at the pressure transducer 152, and $T_G$ is the gas temperature determined by temperature sensor 154.

Figure 10:
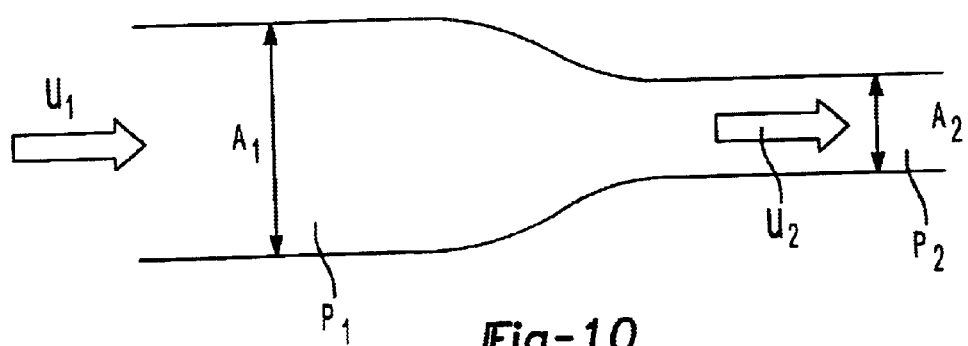
FIG. 10 is a view illustrating the operation of the sixth preferred embodiment of the invention.

With reference to FIG. 10, Bernoulli's equation sets forth as follows:

$$P_1 + \frac{\rho \cdot u_1^2}{2} = P_2 + \frac{\rho \cdot u_2^2}{2}$$

The velocity relationship due to the venturi is defined by the continuity equation which is:

$$u_2 = \frac{A_1}{A_2} u_1$$

where $A_1$ and $A_2$ are bore sizes and the Bernoulli equation is $$\frac{\rho \cdot u_1^2}{2} = P_2 + \frac{\rho \cdot u_2^2}{2} - P_1 \rightarrow u_1^2 = \frac{2}{\rho}(P_2 - P_1) + u_2^2$$

therefore, $$u_1^2 = \frac{2}{\rho}(P_2 - P_1) + \left(\frac{A_1}{A_2}\right)^2 \cdot u_1^2$$

and $$u_1 = \sqrt{\frac{\frac{2}{\rho}(P_2 - P_1)}{1 - \left(\frac{A_1}{A_2}\right)^2}}$$

The mass flow rate in the system can be estimated by the following equation:

$$Q_{pres} = A_1 \cdot u_1 \cdot \rho$$

By measuring the mass flow rate from the gas flow sensor ($Q_{GFS}$) and the evaluation of the flow with the pressure transducers $Q_{press}$, the error between the two detection methods can be evaluated and a compensation factor and gas type can be derived by lookup table or other dynamic method.

From the foregoing, it can be seen that the present invention provides a novel system and method for detecting the type of gas in a gaseous system using two or more sensors, each of which generate output signals representative of a condition of the gas. Once the type of gas has been identified, the hot element mass flow sensor may be calibrated or trimmed in accordance with the then identified gas type.

Having described my invention, however, many modifications thereto will become apparent to those skilled in the art to which it pertains without deviation from the spirit of the invention as defined by the scope of the appended claims.

We claim:

1. A system for identifying a type of gas comprising:
    a first sensor in contact with the gas, said first sensor providing a first electrical output signal indicative of a first condition of the gas,
    a second sensor in contact with the gas, said second sensor providing a second electrical output signal indicative of a second condition of the gas,
    processing means which receives said first and second output signals as input signals for determining the type of gas,
    wherein each of said first and second conditions of the gas are selected from the group of temperature, mass flow rate and pressure.

2. The invention as defined in claim 1 wherein said first sensor comprises a non-linear mass flow sensor having preset temperature compensation for a first predetermined gas type and said second sensor comprises a non-linear mass flow sensor having preset temperature compensation for a second predetermined gas type, said first and second predetermined gas types being different from each other.

3. The invention as defined in claim 1 wherein said first sensor comprises a mass flow sensor positioned in a first bore of a first cross sectional area, said second sensor comprises a mass flow sensor positioned in a second bore of a second cross sectional area different than said first cross sectional area, said first and second bores being fluidly connected in series with each other.

4. The invention as defined in claim 3 wherein said first and second sensors each comprise a non-linear mass flow sensor having preset temperature compensation for a predetermined gas type.

5. The invention as defined in claim 4 wherein both said first and second sensors have said preset temperature compensation for the same gas type, and comprising a temperature sensor in contact with the gas, said temperature sensor producing an electrical output signal proportional to the gas temperature, said temperature sensor output signal being coupled as an input signal to said processing means.

6. The invention as defined in claim 2 wherein said first and said second flow sensors comprise a hot element mass flow sensor, said hot element for said flow sensors being mounted in a common housing.

7. The invention as defined in claim 1 wherein said first sensor comprises a flow sensor having a heated element and said second sensor comprises a temperature sensor which measures the temperature of the gas, means for varying the temperature differential between said heated element and said gas temperature at a constant mass flow rate through said flow sensor.

8. The invention as defined in claim 1 wherein said first sensor comprises a flow sensor having a heated element and said second sensor comprises a temperature sensor which measures the temperature of the gas, a second flow sensor having a heated element, means for maintaining a first temperature differential between said heated element of said first sensor, and means for maintaining a second temperature differential between said heated element of said second flow sensor, said first and second temperature differentials being different from each other.

9. The invention as defined in claim 1 wherein said first sensor comprises a flow sensor having a heated element and wherein said second sensor comprises a pressure sensor.

10. The invention as defined in claim 9 and comprising a temperature sensor which produces an output signal representative of the temperature of the gas, and means for varying the temperature differential between said heated element and the gas temperature.

11. The invention as defined in claim 1 wherein said first sensor comprises a mass flow sensor, said second sensor comprises a pressure sensor positioned in a bore of a first predetermined cross sectional area in series with said mass flow sensor, and a second pressure sensor positioned in a bore of a second predetermined cross sectional area in series with said first bore, said second pressure sensor providing an output signal to said processing means representative of the gas pressure.

12. The invention as defined in claim 1 wherein said processing means comprises a microprocessor having accessible electronic memory, and at least one lookup table stored in said electronic memory.

13. A method for determining the type of gas in a volume of gas comprising the steps of:

measuring a first condition of the gas in the gas volume with a first sensor in contact with the gas, said first sensor providing a first electrical output signal representative of said first condition, measuring a second condition of the gas in the gas volume with a second sensor in contact with the gas, said second sensor providing a first electrical output signal representative of said second condition, and processing said outputs from said first and second sensors to determine the gas type by comparing said sensor outputs with predetermined values, wherein said first and second conditions of the gas are each selected from the group of temperature, mass flow rate and pressure.

14. The invention as defined in claim 13 wherein said first and second conditions each comprise mass flow rate of the gas.

15. The invention as defined in claim 14 and comprising the further step of measuring the temperature of the gas and utilizing the gas temperature as a variable factor in said processing step.

16. The invention as defined in claim 13 wherein one of said conditions comprises the pressure of the gas.

17. The invention as defined in claim 13 wherein one of said conditions comprises the temperature of the gas.

18. The invention as defined in claim 13 wherein said processing step comprises the step of comparing said outputs from said sensors to predetermined tables stored in electronic memory.

19. A system for identifying a type of gas in a gaseous fuel automotive internal combustion engine comprising:

a first sensor in contact with the gas, said first sensor providing a first electrical output signal indicative of a first condition of the gas, a second sensor in contact with the gas, said second sensor providing a second electrical output signal indicative of a second condition of the gas, processing means which receives said first and second output signals as input signals for determining the type of gas, wherein each of said first and second conditions of the gas are selected from the group of temperature, mass flow rate and pressure.

20. A system for identifying a type of gas comprising:

a first sensor in contact with the gas, said first sensor providing a first electrical output signal indicative of a first condition of the gas, a second sensor in contact with the gas, said second sensor providing a second electrical output signal indicative of a second condition of the gas, processing means which receives said first and second output signals as input signals for determining the type of gas, wherein each of said first and second conditions of the gas are selected from the group of temperature, mass flow rate, temperature and pressure.

* * * * *